(12) United States Patent
Cetinkaya

(10) Patent No.: US 12,128,135 B2
(45) Date of Patent: Oct. 29, 2024

(54) INDIVIDUALIZED SOLID DOSAGE PRODUCTS AND A SYSTEM AND METHOD FOR THE GLOBALLY INTEGRATED PHARMACEUTICAL MANUFACTURING AND ITS MONITORING THEREOF

(71) Applicant: Pharmacoustics Technologies LLC, Potsdam, NY (US)

(72) Inventor: Cetin Cetinkaya, Potsdam, NY (US)

(73) Assignee: Pharmacoustics Technologies LLC, Potsdam, NY (US)

( * ) Notice: Subject to any disclaimer, the term of this patent is extended or adjusted under 35 U.S.C. 154(b) by 230 days.

(21) Appl. No.: 16/819,700

(22) Filed: Mar. 16, 2020

(65) Prior Publication Data
US 2021/0038512 A1  Feb. 11, 2021

Related U.S. Application Data

(62) Division of application No. 15/097,994, filed on Apr. 13, 2016, now Pat. No. 10,653,622.

(Continued)

(51) Int. Cl.
*A61K 9/00* (2006.01)
*A61J 3/00* (2006.01)
(Continued)

(52) U.S. Cl.
CPC .............. *A61K 9/0097* (2013.01); *A61J 3/00* (2013.01); *A61K 9/0053* (2013.01); *A61K 9/20* (2013.01);
(Continued)

(58) Field of Classification Search
CPC ...... A61K 9/0097; A61K 9/0053; A61K 9/20; A61K 9/2095; A61K 2/2893; G06N 20/00;
(Continued)

(56) References Cited

U.S. PATENT DOCUMENTS 3,186,910 A    6/1965 Glassman
3,228,789 A    1/1966 Glassman
(Continued)

FOREIGN PATENT DOCUMENTS

BE    900950       4/1985
DE    A-3727894    3/1989
(Continued)

OTHER PUBLICATIONS

Hirshfield, Laura, et al., "Dropwise Additive Manufacturing of Pharmaceutical Products for Melt-Based Dosage Forms," Pharmaceutics, Drug Delivery and Pharmaceutical Technology, Journal of Pharmaceutical Sciences, Feb. 2014, 103:496-506.

(Continued)

*Primary Examiner* — Lauren P Farrar
(74) *Attorney, Agent, or Firm* — Woods Oviatt Gilman LLP; Dennis B. Danella, Esq.

(57) ABSTRACT

A solid dosage product having a tailored dissolution profile comprises a carrier block defining a plurality of compartments where each respective compartment is configured to receive one or more active pharmaceutical ingredient and the carrier block being digestible within an animal such that each respective active pharmaceutical ingredient is controllably released; and one or more coating layers applied to the carrier block. A method for manufacturing a solid dosage product having a tailored dissolution comprises manufacturing a digestible carrier block where the carrier block defines a plurality of compartments with each respective compartment configured to receive an active pharmaceutical ingredient; filling a respective compartment with a respective active pharmaceutical ingredient; and coating the carrier block with one or more coating layers.

10 Claims, 13 Drawing Sheets

Related U.S. Application Data

(60) Provisional application No. 62/178,476, filed on Apr. 13, 2015.

(51) Int. Cl.
  *A61K 9/20* (2006.01)
  *A61K 9/28* (2006.01)
  *B33Y 10/00* (2015.01)
  *B33Y 80/00* (2015.01)
  *G01N 33/15* (2006.01)
  *G06N 3/08* (2023.01)
  *G06N 20/00* (2019.01)

(52) U.S. Cl.
  CPC .......... *A61K 9/2095* (2013.01); *A61K 9/2893* (2013.01); *G01N 33/15* (2013.01); *G06N 3/08* (2013.01); *G06N 20/00* (2019.01); *B33Y 10/00* (2014.12); *B33Y 80/00* (2014.12)

(58) Field of Classification Search
  CPC ............. G06N 3/08; A61J 3/00; G01N 33/15; B33Y 10/00; B33Y 80/00; A61M 37/0069
  See application file for complete search history.

(56) References Cited

U.S. PATENT DOCUMENTS

| | | | |
|---|---|---|---|
| 4,678,516 A | 7/1987 | Alderman et al. | |
| 4,738,724 A | 4/1988 | Wittwer et al. | |
| 4,738,817 A | 4/1988 | Wittwer et al. | |
| 4,764,378 A | 8/1988 | Keith et al. | |
| 4,806,337 A | 2/1989 | Snipes et al. | |
| 5,004,601 A | 4/1991 | Snipes | |
| 5,082,655 A | 1/1992 | Snipes et al. | |
| 5,135,752 A | 8/1992 | Snipes | |
| 5,139,790 A | 8/1992 | Snipes | |
| 5,244,668 A | 9/1993 | Snipes | |
| 5,443,461 A | 8/1995 | Atkinson et al. | |
| 5,672,359 A * | 9/1997 | Digenis ................ | A61K 9/4808 424/463 |
| 5,812,410 A | 9/1998 | Lion et al. | |
| 5,965,167 A | 10/1999 | Sanghvi et al. | |
| 6,962,715 B2 | 11/2005 | Lee et al. | |
| 7,457,685 B2 | 11/2008 | D Silva | |
| 7,707,964 B2 | 5/2010 | Childers | |
| 7,727,576 B2 | 6/2010 | Figueroa et al. | |
| 7,868,260 B2 | 1/2011 | MacMichael et al. | |
| 7,894,882 B2 | 2/2011 | Mullick et al. | |
| 8,022,032 B2 | 9/2011 | Kirsh et al. | |
| 8,074,835 B2 | 12/2011 | MacMichael et al. | |
| 8,383,579 B2 | 2/2013 | Kirsh et al. | |
| 8,828,411 B2 | 9/2014 | Yoo et al. | |
| 8,888,480 B2 | 11/2014 | Yoo et al. | |
| 9,164,032 B2 | 10/2015 | Islam | |
| 10,189,616 B2 | 1/2019 | Kraft | |
| 10,231,932 B2 | 3/2019 | Swinney et al. | |
| 2002/0142035 A1* | 10/2002 | Abrams ............. | A61K 31/7048 424/473 |
| 2003/0200726 A1 | 10/2003 | Rast | |
| 2006/0078621 A1 | 4/2006 | Wedinger et al. | |
| 2012/0041778 A1* | 2/2012 | Kraft ........................ | G16Z 99/00 215/250 |
| 2013/0216616 A1 | 8/2013 | Alfano | |
| 2016/0345906 A1* | 12/2016 | Johnson ................ | A61B 5/1473 |

FOREIGN PATENT DOCUMENTS

| | | |
|---|---|---|
| FR | 28646 | 3/1925 |
| FR | 2524311 | 10/1983 |
| NL | 7610038 | 3/1978 |
| WO | 9012567 | 11/1990 |
| WO | 9516438 | 6/1995 |
| WO | 0108666 | 2/2001 |
| WO | 20047010978 | 2/2004 |
| WO | 2014144512 | 9/2014 |

OTHER PUBLICATIONS

Wilkinson, Grant R., PhD., D.Sc., "Drug Metabolism and Variability Among Patients in Drug Response," The New England Journal of Medicine, 352;21, May 26, 2005, pp. 2211-2221.

Teng, Jaja, et al., "Lack of Medication Dose Uniformly in Commonly Split Tablets," Journal of the American Pharmaceutical Association, vol. 42, No. 2, Mar./Apr. 2002, pp. 195-199.

Van Santen, E., et al., "Breaking of Scored Tablets: A Review," European Journal of Pharmaceutics and Biopharmaceutics, 2002, 53, pp. 139-145.

Thomson, Sarah A., et al., "Minitablets: New Modality to Deliver Medicines to Preschool-Aged Children," Pediatrics, vol. 123, No. 2, Feb. 2009, pp. e235-e238.

Buanz, Asma B. M., et al., "Preparation of Personalized-Dose Salbutamol Sulphate Oral Films With Thermal Ink-Jet Printing," Pharmaceutical Research, Oct. 2011, 28: 2386.

"Table 1: Response Rates of Patients to a Major Drug for a Selected Group of Therapeutic Areas 1," Physicians' Desk Reference, 54th Edition, 2000.

"Pharmaceutical CGMPS for the 21st Century—A Risk-Based Approach—Final Report," Department of Health and Human Services, U.S. Food and Drug Administration, Sep. 2004.

Newberger, Jake, "Future of Pharma Manufacturing is Now," http://www.pharmamanufacturing.com/articles/2013/1306-therapeutic-dose/, Jun. 4, 2013.

Osterberg, Lars, M.D., et al., "Adherence to Medication," The New England Journal of Medicine, 353;5, Aug. 4, 2005, pp. 487-497.

Cutler, David M., et al., "The Value of Antihypertensive Drugs: A Perspective On Medical Innovation," Health Affairs, vol. 26, No. 1, Jan./Feb. 2007, pp. 97-110.

Doshi, Jalpa A., PhD., et al., "Impact of a Prescription Copayment Increase on a Lipid-Lowering Medication Adherence in Veterans," Circulation—Journal of the American Heart Association, Jan. 12, 2009; 119: 390-397.

Mosen, David M., PhD., MPH, et. al., "Is Patient Activation Associated With Outcomes of Care for Adults With Chronic Conditions?," Journal of Ambulatory Care Management, vol. 30, No. 1, Jan.-Mar. 2007, pp. 21-29.

Stein, Rob, "Shortages of Key Drugs Endanger Patients," The Washington Post, May 1, 2011, 6 pages.

Ponchel, Gilles, et al., "Specific and Non-Specific Bioadhesive Particulate Systems for Oral Delivery to the Gastrointestinal Tract," Elsevier Science B.V., Advanced Drug Delivery Reviews 1998, vol. 34, pp. 191-219.

Thompson, Cheryl A., "Stakeholders in Supply Chain Discuss Shortages," American Journal of Health-System Pharmacy, News Section, vol. 68, Jan. 1, 2011, pp. 9-10.

Ventola, C. Lee, MS, "The Drug Shortage Crisis in the United States: Causes, Impact, and Management Strategies," P & T, Nov. 2011, vol. 36, No. 11, pp. 740-757.

Gates, Bill, "The Next Epidemic—Lessons from Ebola," The New England Journal of Medicine or NEJM.org, Perspective Section, vol. 372, No. 15, Apr. 9, 2015, pp. 1381-1384.

Cutler, David M., Ph.D., et al., "Thinking Outside the Pillbox—Medication Adherence as a Priority for Health Care Reform," The New England Journal of Medicine or NEJM.org, Perspective Section, vol. 362, No. 17, Apr. 29, 2010, pp. 1553-155.

Taylor, Phil, "Top 5 Reasons for a Class I Product Recall," www.pharmafile.com/news/154814/top-5-reasons-class-i-product-recall, pp. 1-5, Apr. 21, 2011.

Fox, Erin R., et al., "ASHP Guidelines on Managing Drug Product Shortages in Hospitals and Health Systems," American Journal of Health-System Pharmacy, ASHP Report Section, vol. 66, Aug. 1, 2009, pp. 1399-1406.

Woodley, John, Dr., "Bioadhesion New Possibilities for Drug Administration?," Clin Pharmacokinet 2001; 40(2), Adis International Limited, pp. 77-84.

(56) References Cited

OTHER PUBLICATIONS

Spear, Brian B., et al., "Clinical Application of Pharmacogenetics," Trends in Popular Medicine, vol. 7., No. 5, May 2001, pp. 201-204.

"Drug Shortages: Current Drugs," http://www.ashp.org/menu/DrugShortages/CurrentShortages, 2016 American Society of Health-System Pharmacists (ASHP), Apr. 27, 2016, pp. 1-6.

Nagaich, Upendra, et al., "Drug Recall: An Incubus for Pharmaceutical Companies and Most Serious Drug Recall of History," International Journal of Pharmaceutical Investigation, http://www.ncbi.nlm.nih.gov/pmc/articles/PMC4286830/?report=printable, Jan.-Mar. 2015; 5(1): 13-19, pp. 1-11, Medknow Publications.

Orlovich, Daniel S., PharmD, et al., "Drug Shortages in the U.S.—A Balanced Perspective," APSF Newsletter—The Official Journal of the Anesthesia Patient Safety Foundation, vol. 29, No. 3, 41-64, Feb. 2015, pp. 49-50.

American Society of Health-System Pharmacists (ASHP), et al., "Drug Shortages Summit Nov. 5, 2010 Summary Report," Hyatt Regency, Bethesda, Maryland, Nov. 5, 2010, pp. 1-52.

Jensen, Valerie, et al., "FDA's Role in Responding to Drug Shortages," American Journal of Health-System Pharmacy, Special Feature Section, vol. 59, Aug. 1, 2002, pp. 1423-1425.

Lewis, Jonathan M., et al., "How to Effectively Manage a Product Recall," http://www.pharmtech.com/how-effectively-manage-product-recall, vol. 35, Issue 1, Jan. 2, 2011, pp. 1-5.

Peppas, Nikolas A., et al., "Hydrogels as Mucoadhesive and Bioadhesive Materials: A Review," Elsevier Science B.V., Biomaterials 1996, vol. 17., No. 16, pp. 1553-1561.

Lazarou, Jason, MSc, et al., "Incidence of Adverse Drug Reactions in Hospitalized Patients—A Meta-Analysis of Prospective Studies," http://jama/jamanetwork.com/on09/03/2012, The Journal of the American Medical Association (JAMA), Apr. 15, 1998, vol. 279, No. 15, pp. 1200-1205.

"Introducing the New Xcelodose S—New Powder Micro-Dosing System," www.capsulgel.com, May 2008, 5 pages.

Katstra, W.E., et al., "Oral Dosage Forms Fabricated by Three Dimensional Printing," Journal of Controlled Release, 66 (2000), pp. 1-9.

"Pandemic Risk and One Health," http://www.worldbank.org/en/topic/health/brief/pandemic-risk-one-health, The World Bank, Oct. 23, 2013 (Last Updated Jan. 2014), pp. 1-5.

Chapman, Richard H., Ph.D., et al., "Predictors of Adherence With Antihypertensive and Lipid-Lowering Therapy," Arch Intern Med, vol. 165, May 23, 2005, (www.archinternmed.com; http://archinte.jamanetwork.com/byXiaochiXu), Original Investigation section, pp. 1147-1152.

"Report on the ISPE Drug Shortages Survey," Jun. 2013, www.ISPE.org/drugshortages/2013JuneReport, pp. 1-24.

Cuff, George, et al., "A Preliminary Evaluation of Injection Molding as a Technology to Produce Tablets," Pharmaceutical Technology, Jun. 1998, pp. 96-106.

Wald, NJ, et al., "A Strategy to Reduce Cardiovascular Disease by More Than 80%," British Medical Journal, vol. 326, Jun. 28, 2003, pp. 1419, 1423, and 1427.

Blau, Gary E., et al., "Validation of a Novel Approach for Dose Individualization in Pharmacotherapy Using Gabapentin in a Proof of Principles Study," Pharmacotherapy, vol. 33, No. 7, 2013, pp. 727-735.

\* cited by examiner

INDIVIDUALIZED SOLID DOSAGE PRODUCTS AND A SYSTEM AND METHOD FOR THE GLOBALLY INTEGRATED PHARMACEUTICAL MANUFACTURING AND ITS MONITORING THEREOF

CROSS-REFERENCE TO RELATED APPLICATIONS

This application is a divisional of U.S. patent application Ser. No. 15/097,994, filed on Apr. 13, 2016, which claims the benefit of U.S. Provisional Application No. 62/178,476, filed Apr. 13, 2015, both of which are incorporated herein by reference in their entireties.

BACKGROUND OF THE INVENTION

The present invention relates to individualized, customized and personalized solid dosage products having combined doses of one or more drugs that may have a tailored dissolution profile, more particularly to solid dosage products comprising one or more drugs and various sensors or other devices; and to a system and method for the monitoring and calibration of a global network of production units and machines manufacturing the solid dosage products, as well as the real-time monitoring and qualifying of the solid dosage products being produced.

Combining one or more small molecule active ingredients, e.g., active pharmaceutical ingredients (APIs) such as drugs, into one delivery system is becoming a generally accepted approach to providing enhanced treatment of certain diseases or as a method for increasing compliance with, or timelier uptake of, a second drug which complements the first drug. Currently these combinations are manufactured by a pharmaceutical company or a compound pharmacy as a unitary pill or tablet having fixed concentrations of each drug in the final product, often referred to as a polypill. A distributor may then ship supplies of each finished product to a dispensing group such as a pharmacy and/or an end-user. Then, based on a script written by a healthcare provider or under the direction of a healthcare provider, the pharmacy dispenses these tablets, capsules, pills, ointments, and the like to the patient. To be financially worthwhile for a drug manufacturer, a particular drug/dosage permutation would need to prove suitable for a large number of people. As a result, currently manufactured polypills lack much individualization and are genericized so as to capture a greater percentage of the population. Nonetheless, personalized polypills may be manufactured through custom-compounding by a pharmacist; however, very few pharmacies offer such a service.

A further limitation of current polypills is that commercially available medicines are generally available having active ingredients in only a few discrete doses. Consumers need to take one or more tablets of an available dosage so as to roughly receive a desired amount of the active ingredient. In cases where delivery of a precise dose is paramount, such as for highly potent actives, drugs with a narrow therapeutic index, or pediatric formulations (where the dose is based on body mass), the commercial tablets may need to be physically split or otherwise divided prior to administration. However, dividing tablets may result in inaccurate and unknowable amounts of active ingredient within each of the various resultant pieces. As such, consumers can only assume that they are getting the desired amount of active ingredient, but may, in fact, be under-dosing or over-dosing when consuming one piece of the divided tablet.

Another drawback to current medications and its utilization is the poor adherence to treatment regimens by patients. As many as half of all patients do not adhere faithfully to their medication regimens resulting in more than $100 billion spent each year on avoidable hospitalizations. For patients with coexisting conditions who take multiple medications prescribed by multiple physicians, there is also a vital need to reconcile the prescribed regimen with what a patient is actually taking and to understand why there is a difference between the two. However, optimizing and reconciling medications requires substantial investments of time by a skilled health care practitioner, as well as electronic data sharing among practitioners, neither of which is widely available in today's model of health care delivery. Moreover, there are also numerous other factors that affect adherence at the individual level, including lifestyle, psychological issues, health literacy, support systems and side effects of the medications. Indeed, patients' personal attributes probably have the strongest influence on adherence. Thus, engaging, supporting and monitoring patients to improve adherence may improve health outcomes.

Accordingly, there exists a need for a system, method and product harnessing the rapidly converging features of 3D printing/additive solid dosage drug manufacturing, digital medicine with embedded sensors and electronic devices; and personalized medicine dosing. The present invention addresses these and other needs.

SUMMARY OF THE INVENTION

Individualized medicine is an emerging focus in pharmaceuticals in which a dosage regimen is determined for a patient based on that patient's specific therapeutic response to active pharmaceutical ingredients (APIs), such as but not limited to drugs, proteins, peptides or other small molecules, nutritional supplements, vaccines and/or gene therapies. Currently, the determination of the most appropriate regimen is carried out by physicians via trial and error beginning with a nominal dosage. Predicting a regimen that has the highest probability of meeting the therapeutic needs of a patient may be optimized through use of pharmacokinetic and pharmacodynamic models and parameter distributions determined from population clinical data coupled with a limited number of plasma samples from a given patient. Additive manufacturing of pharmaceutical products may allow for the production of solid dosage products having a predicted dosage of select API(s). Such products may be utilized at a compounding pharmacy or clinic. Thus, tablets would not need to be mass produced in multiple variations of dosage loading. Creating and monitoring dosage forms via this process in the compounding pharmacy also mitigates potential issues with stability of APIs as it reduces the time between manufacturing and patient consumption.

In one aspect of the present invention, a method may involve manufacturing a series of API formulations in physical forms which can be combined as per a physician's prescription; stockpiling those forms while identifying the concentration of each of two or more APIs which are tailored to treat a particular patient's unique metabolism and one or more diseases; communicating that information to a producer, where the producer then combines the individual concentrations of each API into single unit solid dosage products, such as tablets, capsules or pills, and distributes those indirectly or directly to the patient.

Additional objects, advantages and novel features of the present invention will be set forth in part in the description which follows, and will in part become apparent to those in the practice of the invention, when considered with the attached figures.

BRIEF DESCRIPTION OF THE DRAWINGS

The accompanying drawings form a part of the this specification and are to be read in conjunction therewith, wherein like reference numerals are employed to indicate like parts in the various views, and wherein.

DETAILED DESCRIPTION OF THE INVENTION

Figure 1:
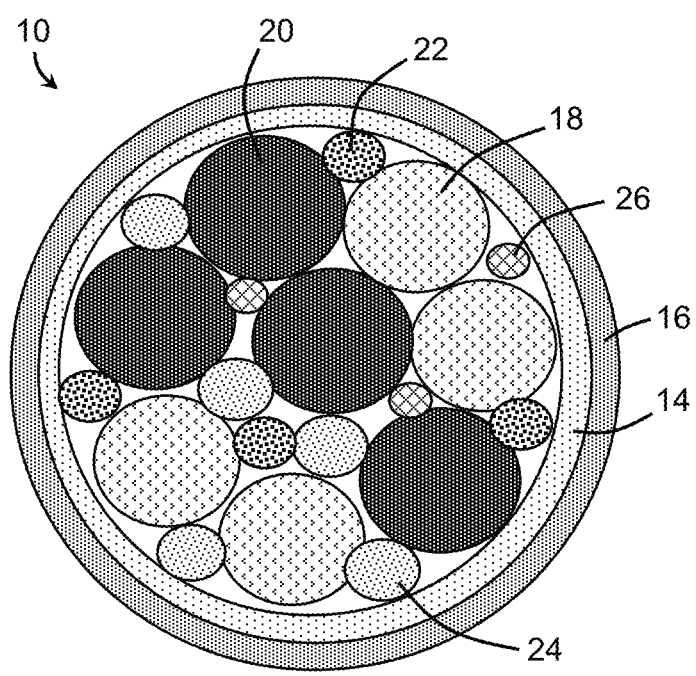
FIG. 1 is a schematic of a representative solid dosage product in accordance with the present invention.

Referring now to the drawings in detail, FIG. 1 depicts a solid dosage product, such as a tablet 10. The most fundamental and critical objective of a tablet is to deliver the active ingredient into the human blood stream accurately and reproducibly. Essentially, a tablet should be considered as a consumable drug delivery device. Tablet 10 may consist of two basic structural parts: (i) a core 12 and (ii) one or more coating layers 14, 16. Core 12 of tablet 12 may contain a mixture of one or more active pharmaceutical ingredients (APIs) 18, 20, along with a number of inactive ingredients identified generally as excipients, an include compounds such as diluents 22, binders 24 and lubricants 26. Currently available tablets generally consist of one API with one or more excipients; the main reasons for formulating a tablet with excipients ranging from management of small dosage amounts of active ingredient to aesthetic reasons, such as the color and shape of a final pharmaceutical product. As a result, tablet 10 is a mechanical system consisting of various bonded functional and structural parts (e.g. core 12 and coating layers 14, 16).

Figure 2:
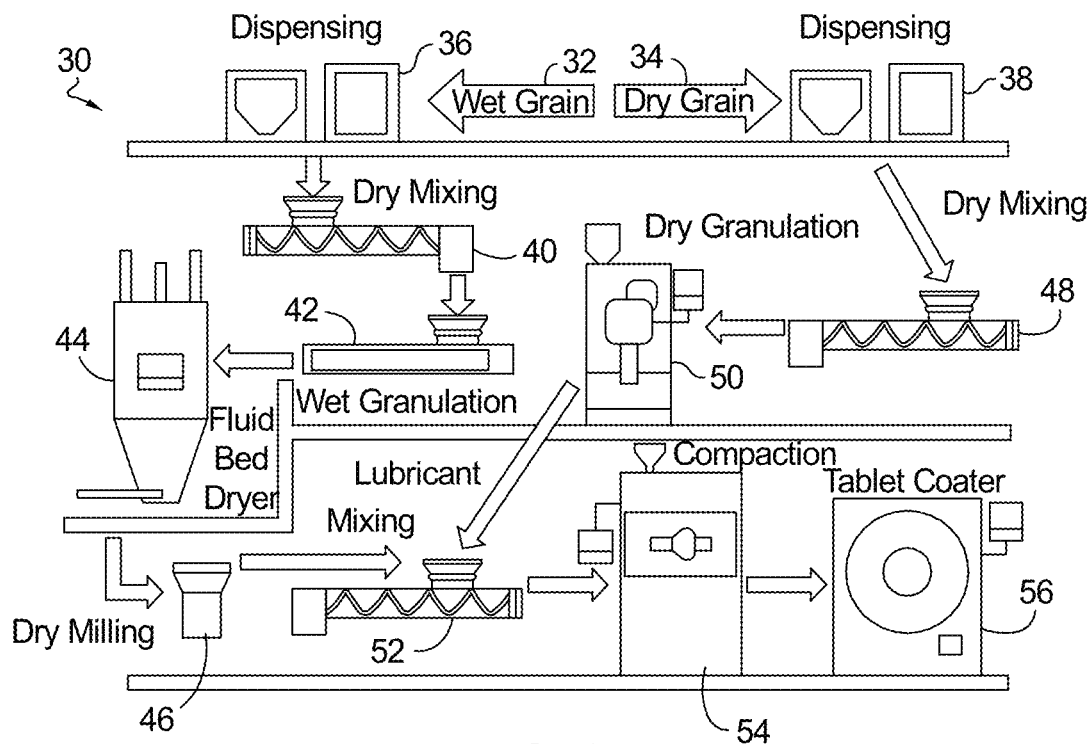
FIG. 2 shows batch processing used to produce solid dosage products.

FIG. 2 shows a flow chart for a batch process 30 for manufacturing solid dosage products, such as a tablet 10. Manufacturing techniques play a major role in the structure of tablet and, consequently, its mechanical/chemical properties and resultant form (with geometric irregularities and defect formation). Initially, wet ingredients 32 and dry ingredients 34 are loaded into respective dispensing units 36, 38. Wet ingredients 32 may then be mixed by a wet mixer 40, granulated by granulator 42 and dried in dryer unit 44 before being size-reduced by dry mill 46. Similarly, dry ingredients 34 are dispensed to dry mixer 48 before passing to dry granulator 50. The dried ingredients from mill 46 and dry granulator 50 may then be mixed in mixer 52. Tablet cores are manufactured at tablet compaction press 54 by applying pressure to the powder mix (from mixer 52) into a (porous) coherent/solid form.

Compaction imparts the physical and mechanical/elastic properties to the tablets, such as density or mechanical strength. These properties determine tablet dissolution properties, integrity and drug bioavailability. The uniaxial compaction of a pharmaceutical powder results in an anisotropic and heterogeneous tablet with variations in such properties as density, porosity and mechanical strength throughout the tablet. Even at relatively high compaction pressures, tablets are considered porous, with the tablet porosity of most materials being about 5 to 30%. Under compression, bonds are established between the particles or granules, and as a result, a form is shaped and a certain mechanical strength is given to the compact. The functional and structural properties of the tablet (e.g. mechanical properties, disintegration time and drug release characteristics) are affected by both the properties of the constituent materials and the manufacturing process. Excipients such as diluents, binders and lubricants are generally needed in a formulation in order to facilitate the manufacturing process, but also to ensure that the resulting tablets have the desired properties. The final stage is the application of coating at tablet coater 56 prior to packaging.

Figure 3:
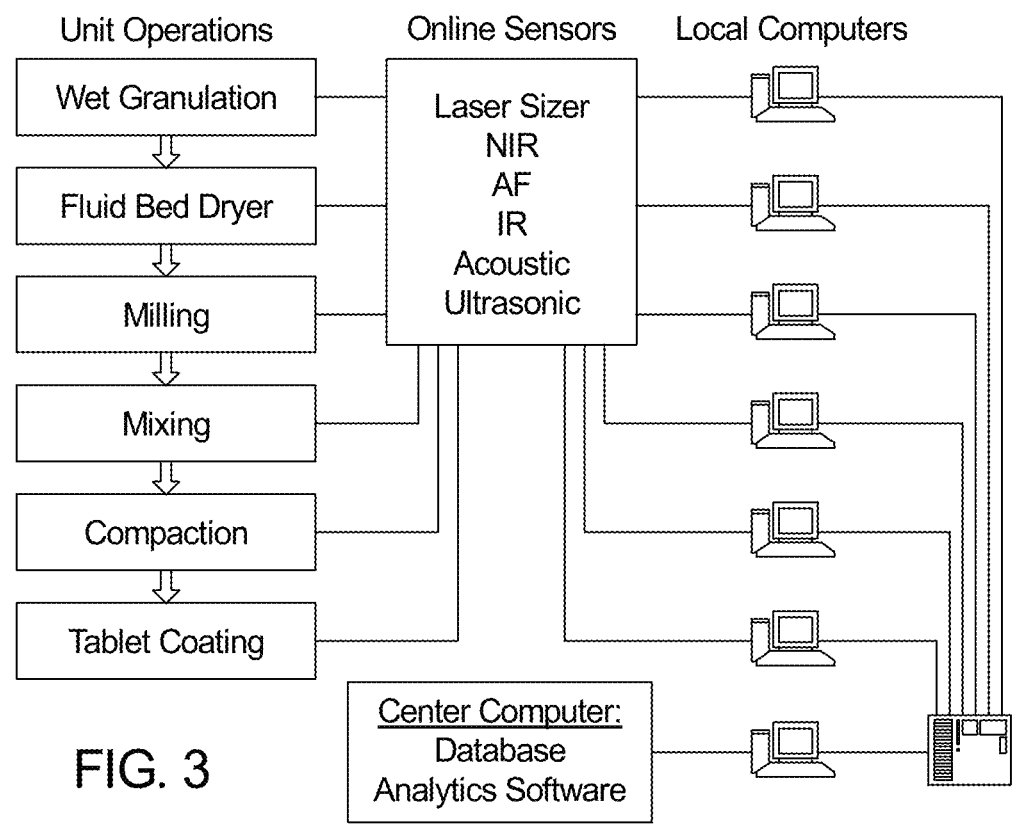
FIG. 3 is an schematic of forming a solid dosage product through a multistage process (unit operations) using sensor data and a central computing unit.

As can be seen in FIG. 2, a manufacturing system may consist of a process chain with each process having a number of operations. In the chain, processes may be linked one-to-one, disjunctively or conjunctively to preceding or subsequent processes. As seen in FIG. 3, manufacturing systems may incorporate computer operated controls and various chemical and physical sensors to ensure proper operation and production. Nevertheless, even in advanced manufacturing systems, there is always a degree of variation of the input parameters of individual intermediate products during the various manufacturing processes. As the processes are dependent on each other, these variations could be tolerable from an individual (isolated) process perspective, but may still lead to an unacceptable accumulation causing failure of the final product to meet the final product requirements. As process quality in manufacturing is directly connected to product quality, improvements of the manufacturing processes can impact qualities, such as efficiency improvements and/or product quality enhancements. As shown in FIG. 3, at each point within a manufacturing system, information as well as physical parts may be exchanged between the interfacing processes. As processes become increasingly more complex, the handling and utilization of information plays an important role in the management of product and process quality. Tracking individual intermediate products along the path of the manufacturing system, and managing each intermediate products quality, is relevant, thus leading to large data sets.

Figure 4:
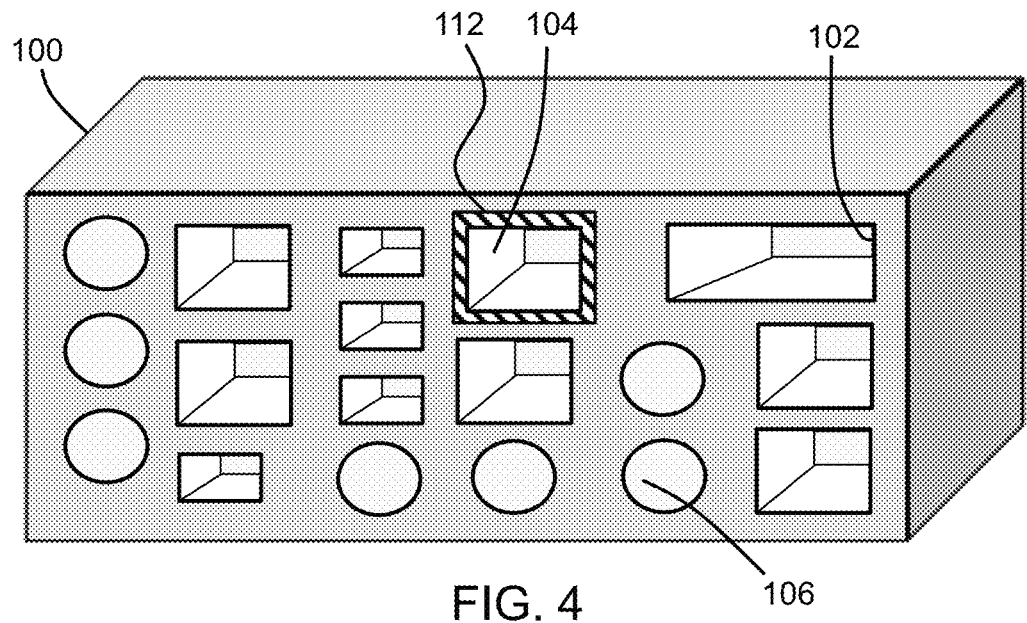
FIG. 4 is a schematic of a carrier block for use within a solid dosage product in accordance with an aspect of the present invention.
Figure 5:
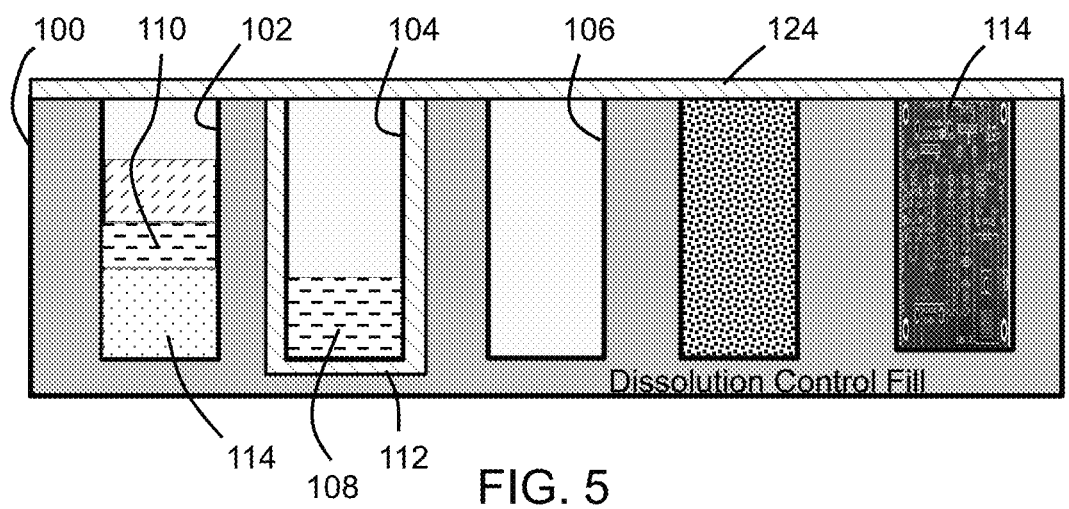
FIG. 5 is a schematic of a side cross-sectional view of a carrier block.
Figure 6:
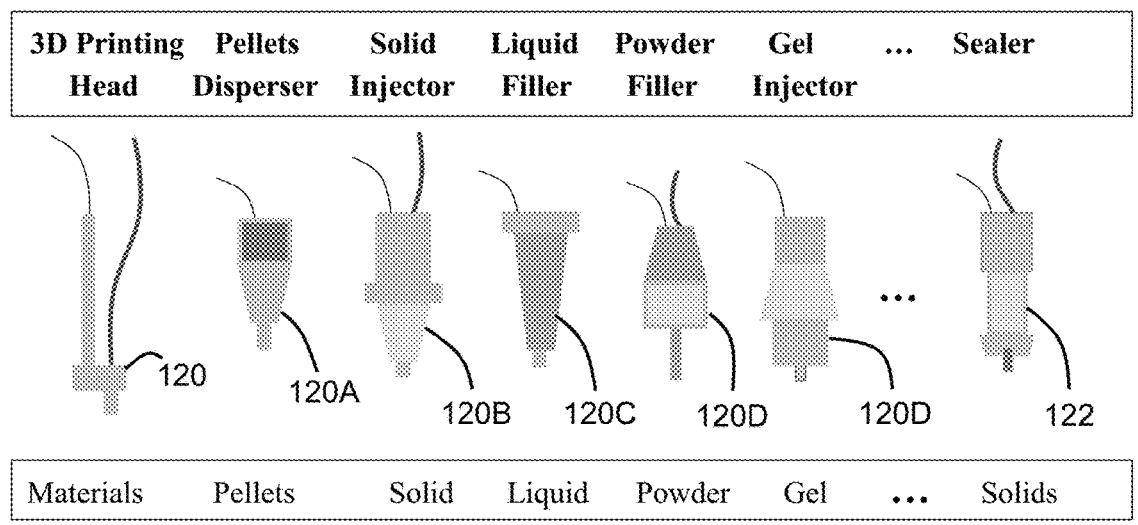
FIG. 6 is a schematic showing a variety of filler heads that may be used to fill a carrier block to manufacture a solid dosage form shown in FIGS. 4 and 5.

Turning now to FIGS. 4 and 5, an embodiment of a core solid dosage carrier block 100 is shown. In one aspect of the present invention, core solid dosage carrier block 100 is fabricated of a digestible, water-solvable material with known in vivo dissolution properties, such as but not limited to starch-based materials, and is configured to be incorporated within additional materials so as to result in a final solid dosage unit, such as a tablet similar to tablet 10. Carrier block 100 may be fabricated through additive manufacturing (AM) methods designed to produce three-dimensional (3D) objects, such as via 3D printing head 120 as seen in FIG. 6. By placing material only where it is needed, in an additive, layer-wise fashion, it is possible to create very complex, internal product architectures that enhance the functionality of a product. By changing the composition of the material from place to place within the product, it is possible to create functionally graded features or to place different materials in different locations to serve radically different functions. As a result, carrier block 100 may be designed and fabricated to include one or more compartments 102, 104, 106 defined in at least one surface of the carrier block 100 so as to allow for provision of a final solid dosage product having individualized dosing of two or more individual active pharmaceutical ingredients (APIs) 108, 110.

If desired, a dissolution profile may be created by using fabrication materials with differing dissolution properties. By way of example, compartment 104 may be fabricated to include an inner layer 112 which may dissolve later than the remainder of the material forming the bulk of carrier block 100. In this manner, an API, such as API 108, resident within compartment 104 may be selectively released in vivo some time after release of API 110. A compartment 102, 104, 106 of carrier block 100 may be configured to receive an electronic element 114 which may monitor and report patient usage of the medication in accordance with his or her treatment regimen as discussed in greater detail below. Electronic element 114 may also include, without limitation thereto, such devices as a wireless transmitter configured to communicate with an external receiver, a remotely activated device triggered by an external device, a logging device activated upon ingestion or upon dissolution of the respective compartment holding device 114, or a patient bonding device configured to aid adhesion of tablet 10 and/or carrier block 100 to the internal surface of the patient.

In a further aspect, micro-encapsulated API particles may instead provide separation on the particle-level so as to achieve the desired sustained/delayed release characteristics. Further note that controlled-release or inter-drug separation might be achieved inherently if excipient blending or granulation is employed for some simple formulation. Such possibilities could also help control taste, when capsules are expected to be re-opened for consumption rather than being swallowed whole. Embodiments may further use additional means of achieving sufficient separation, such as exploiting hydrophobicity/hydrophilicity or using pellets or nanoparticles.

In an aspect of the present invention, apart from the selective fabrication of carrier block 100 to produce a carrier block having a desired dissolution profile, the dosing and dissolution profile of the solid dosage product may further be tailored to an individual patient's needs by selectively filling compartments within carrier block 100 using a plurality of filling heads as shown in FIG. 6. By way of example, various filler heads 120A-120E may be used to fill one or more compartments 102, 104, 106 within carrier block 100. 3D printer head 122 may be used to form a top layer 124 configured to seal the carrier block 100 after carrier block 100 has been selectively filled with desired fill materials. It should be noted that 3D print head 120 may also be used to create the top layer 124.

Each filler head 120A-120E may be computer controlled/monitored and fed materials with various types of feeder cartridges. APIs and excipients can be in various phases such as solids (pellets 120A, powder 120D, etc.), liquid 120C, and emulsions/gels 120E, as well as sensors and devices 114 (device feeder cartridge not shown). In one aspect of the invention filler heads 120A-120E are coordinated to selectively load carrier block 100. By way of example, each filler head may be mounted onto a respective dispensing arm (not shown) such that multiple frequently-used APIs may be preloaded within filler heads, where some of which could remain on "stand-by" during any given prescription when not among the APIs selected for loading. Each filler head may be configured to travel to each compartment or carrier block 100 may travel to selected filler heads 120A-120E. With these approaches, a microbalance integrated with the manufacturing line may weigh the carrier block 100 as it is being filled so as to continuously calculate the subset of weight attributable to each additional drug being dispensed in succession. Alternatively, the microbalance may be re-tared between successive filler heads such that the weight measured by the balance is solely for the material currently being dispensed. Additional coordination and control algorithms may be included to handle issues of sequence management, non-interference, etc.

Figure 7:
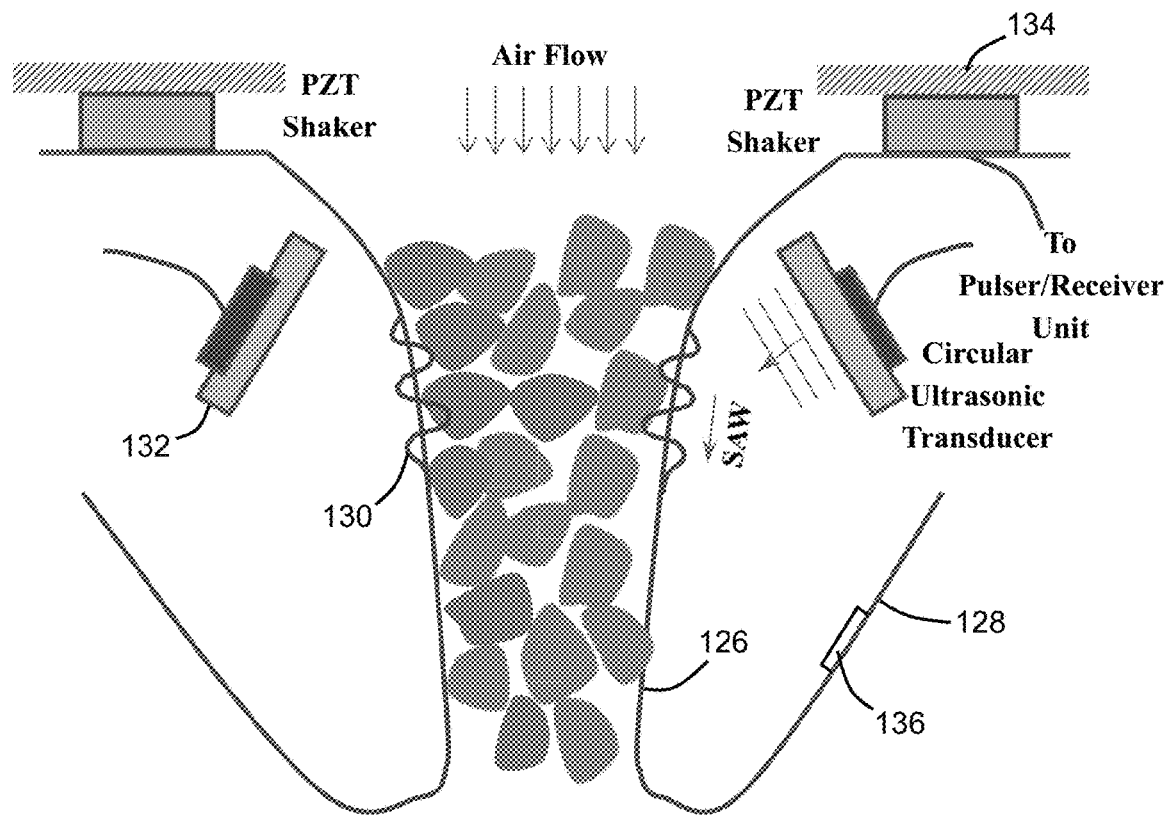
FIG. 7 is a detailed schematic of an acoustic filler head.

By way of example and by no means limiting solely thereto, filler head 120C may be an ink-jet type injector configured for spraying or jetting liquid drops of fluid API-in-solution. A nozzle design and a nanoparticle coating process for increasing flowability of powders, such as with filler head 120D, is shown in FIG. 7. As seen in FIG. 7, wall 126 of the nozzle 128 are excited by SAW (surface acoustic waves) 130 produced by transducer 132 and/or base excitations vibrations generated by one or more piezoelectric devices 134. Surface temperature of nozzle 128 may be controlled and maintained by temperature regulators 136. As a result, micro-dosing enables loading of API formulations, with or without select excipients if desired, with significantly less mass than would otherwise be needed without micro-dosing. For a given dosage (a set of APIs with certain amounts specific to the patient needs) and a specific dissolution profile, the dissolution simulation and Computer Aided Design (CAD) program may determine and optimize the amounts and locations of the all the compartments and filling materials (such as APIs, excipients, sensors, etc.) for the individual patient's healthcare needs.

It should be noted that one of the major problems with formulating protein drugs as oral solid dosage forms is the poor absorption of protein in the gastrointestinal tract. Bioadhesion (and mucoadhesion) is the process whereby synthetic and natural macromolecules adhere to mucosal surfaces in the body. Thus, in accordance with an aspect of the present invention, carrier block 100 may be fabricated, or one or more cavities may be included within carrier block 100 so as to include these macromolecules. As a result, drug absorption by mucosal cells may be enhanced or the drug released at the site for an extended period of time. These muco-adhesive systems are known to provide intimate contact between dosage form and the absorptive mucosa, resulting thereby in high drug flux through the absorbing tissue. Synthetic polymers may include one or more of the following classes of compounds: a chitosan, carbopol or carbomer.

Another related use is in conjunction with blister-packing or the like (which is often required for solid dosages of nursing-home patients). In accordance with an aspect of the present invention, a solid dosage product having multiple active pharmaceutical agents, such as for use with nursing-home patients or hospital outpatients having high pill-burden, may be packaged within compliance-package blister-packs. This blister packaging may further designate a single tablet to be taken at particular time(s) or with a particular meal(s) each day. In this manner, a patient may be able to take only a single product at a clearly defined time rather than being required to take multiple products at varying times throughout the day. This, accordingly, may increase ease of use and patient compliance.

In a further aspect of the present invention, one or more small, ingestible sensors and devices may be attached or embedded within a solid dosage product, such as tablet 10, wherein each sensor may, for instance, emit an identifier number from inside a patient, providing a detailed record of what medications were taken and when. In this manner, each tablet 10 may contain one or more miniature sensors that can communicate, via a digital health feedback system, vital information about the patient's medication-consuming behaviors and how his/her body is responding to the medicine.

Figure 8:
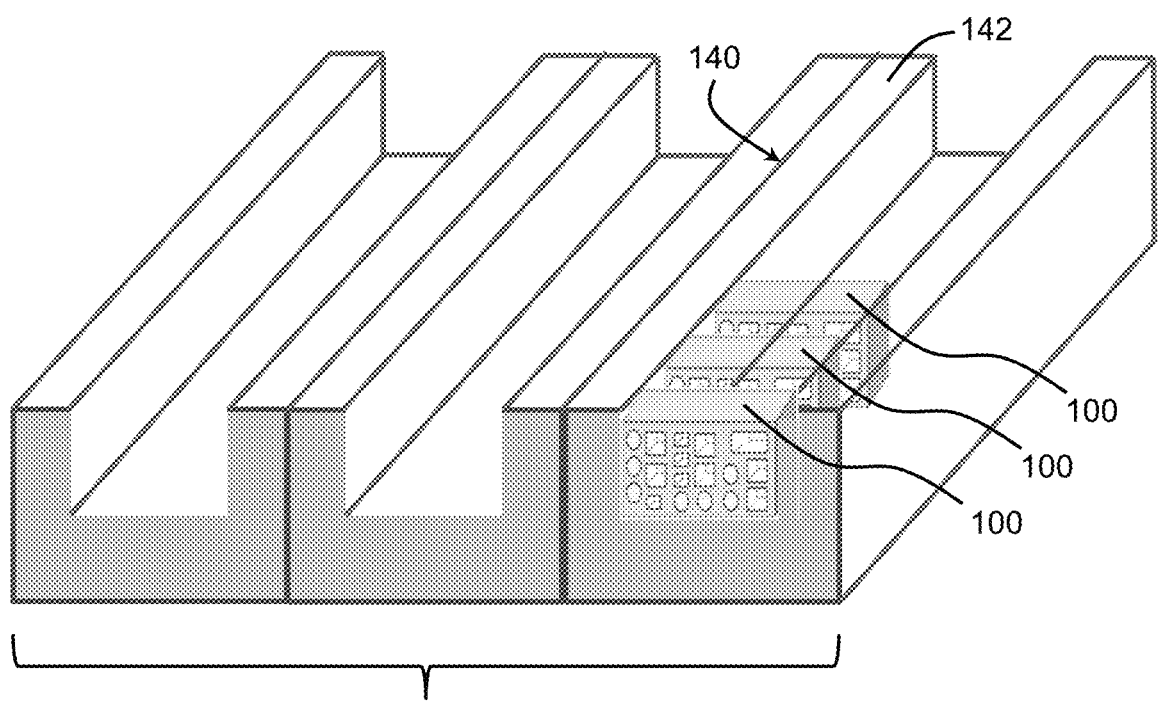
FIG. 8 is a schematic of a carrier block holder in accordance with an aspect of the present invention.

Turning now to FIG. 8, a carrier block holder 140 is shown. Carrier block holder 140 may be configured to hold a plurality of carrier blocks 100 during manufacture. For instance, a one-dimensional array 142 may be used or a block matrix 144 may can be utilized to hold carrier blocks 100 in place during processing. During manufacturing, each carrier block 100 in holder 140 may be first filled with various types of APIs, excipients controlling dissolution profiles, and active devices as described above.

In manufacturing metrology, two primary methodologies are used to evaluate the performance of a machine and/or a process: (1) through a series of direct measurements of machine and process characteristics, and (2) through measurements of products and standardized test artifacts (STAs), which will be discussed in greater detail below, see for instance, FIG. 11. Direct measurements require positioning and/or control of individual machine components, which is often difficult or impossible, either because the moving components are not accessible to the end user or safety controls for potential hazards prevent the user from operating the machine with the measuring instruments in the way. Therefore, STAs may be used in diagnosing and characterizing machines, processes and the resultant intermediate and final products. Careful designs for test artifacts can allow performance assessment of individual machine components. Manufacturing a test artifact enables a composite test, as most errors present in the machine and the process contribute to errors in the STA. The disadvantage of composite tests is that linking specific STA errors to specific machine and/or process error sources often requires the use of models. However, the advantages of STAs are that producing parts is directly aligned with the actual purpose of the manufacturing machine and specialized measuring equipment is rarely necessary since the required equipment is already commonly available in discrete part manufacturing environments. The clear benefit of a standardized part is that different machines or processes that produce the same standardized part can be readily compared. Also, if designed properly, the STAs can test the limitations of the machine or process and be used to identify areas for improvement. Such parts can serve as a method for performance verification between end-users and vendors, as well as provide a platform for vendors to demonstrate improvements in their machines. STAs can be utilized for quantitatively evaluating the performance of a manufacturing machine and/or processes.

The increasing demand for quality of design and control of manufacturing steps, with the goal of ensuring the final product quality, are further required by Process Analytical Technology (PAT), which was launched by the U.S. Food and Drug Administration (FDA) in 2003. According to FDA, PAT is a system for designing, analyzing, and controlling manufacturing through timely measurements (i.e., during processing) of critical quality and performance attributes of raw and in-process materials and processes with the goal of ensuring final product quality. It is important to note that the term analytical in PAT is viewed broadly to include chemical, physical, microbiological, mathematical, and risk analysis conducted in an integrated manner. In addition, in January 2015, FDA created Office of Pharmaceutical Quality (OPQ), a single unit dedicated to product quality. OPQ's main mission is to provide better alignment among all drug quality functions at FDA, including review, inspection, and research. According to FDA, OPQ creates a uniform drug quality program across all sites of manufacture, whether domestic or foreign, and across all drug product areas—new drugs, generic drugs, and over-the-counter drugs.

Utilizing a low latency network of powerful chemometric instruments, multivariate data analysis software, process control tools and a central Structured Query Language (SQL) database, PAT may comprise a flexible system capable of keeping pace with the rapid advances in drug development and manufacture. At the core of any PAT system is a set of Critical Process Parameters (CPPs) that are defined based on the manufacturing equipment itself, functioning as the independent variables along the production line. By monitoring physical and chemical properties, a manufacturer can also define a set of variable CPP-dependent variables known as Critical Quality Attributes (CQAs) at various stages of the process. As a result, the manufacturer may better understand and control the entire manufacturing process so as to produce a desired product meeting predetermined quality control standards. CPPs and CQAs may be used in conjunction with a PAT platform to create both unit-level and high-level process line models capable of predicting the precise quality of the end product. After the predictions are made, adjustments can be fed back into integrated control systems so as to enable fine-tuning of the manufacturing process to further improve product quality and ensure product consistency. PAT platforms have been developed by automation industry leaders, such as Siemens, and current PAT solutions are supported by a vast number of major analyzer manufacturers, such as Mettler Toledo, Thermo Scientific, Kaiser Optical Systems, and the Bruker Corp.

Examples of instruments and analytical processes that may be employed during PAT may include the following: Raman Spectroscopy; X-Ray; Nuclear Magnetic Resonance (NMR); Terahertz Pulsed Imaging; Laser Induced Breakdown Spectroscopy; Acoustic Emission (AE); acoustic resonance; Air-coupled Acoustic Testing/Characterization; Contact Ultrasonic Testing (during and after Compaction); Photo-acoustics Testing/Characterization (Thermomechanical excitation, Piezoelectric sensing); Near Infra-Red (NIR); Ultrasound Testing (during and after Compaction); Tera-Hertz Pulsed Imaging (pulsed electromagnetic waves); and Micro-Thermal Probe Technique. An appropriate combination of some, or all, of these tools may be applicable to a single-unit operation, or to an entire manufacturing process and its quality assurance.

Figure 9:
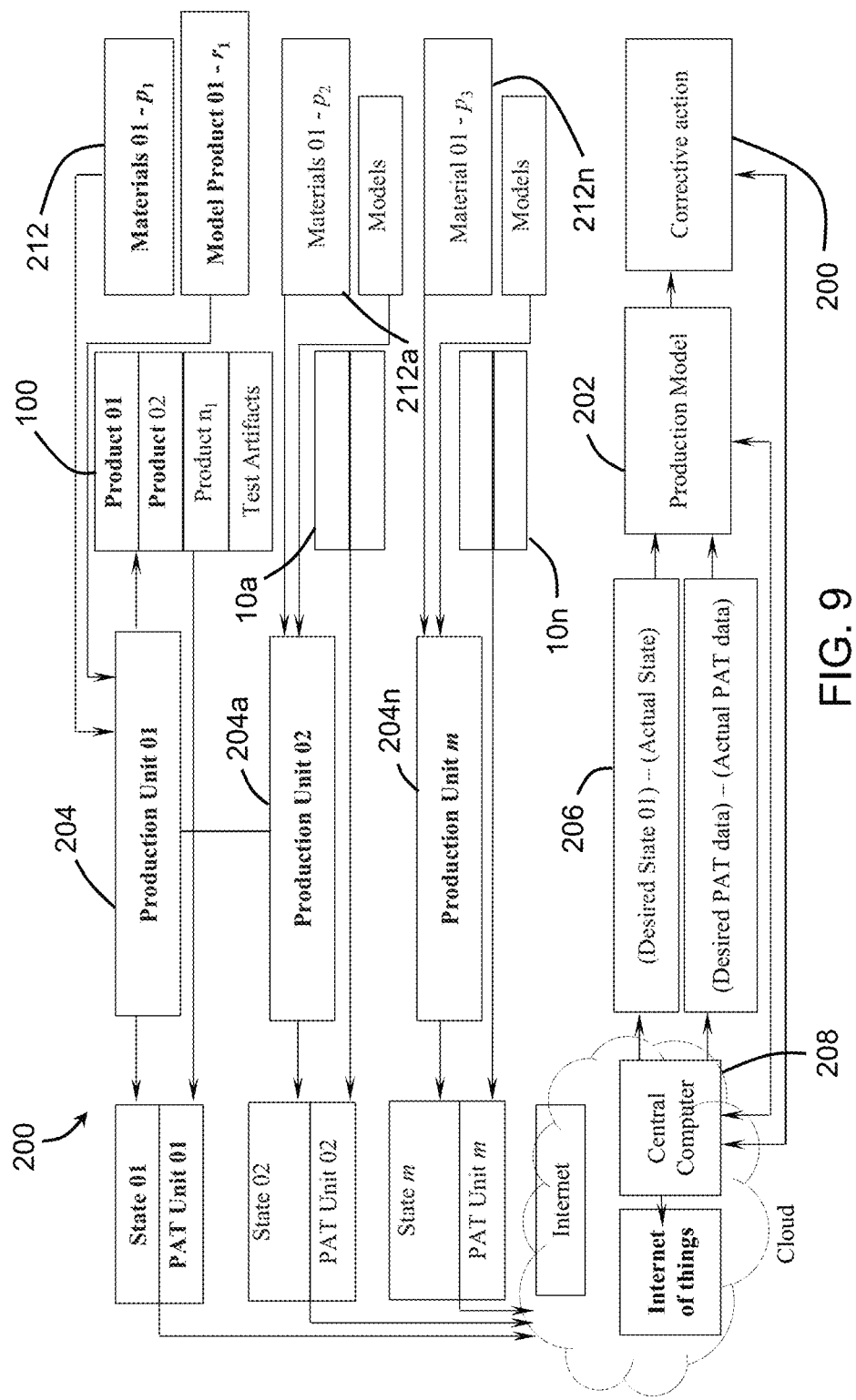
FIG. 9 is a schematic of a cyber-manufacturing machinery architecture in accordance with an aspect of the present invention.
Figure 10:
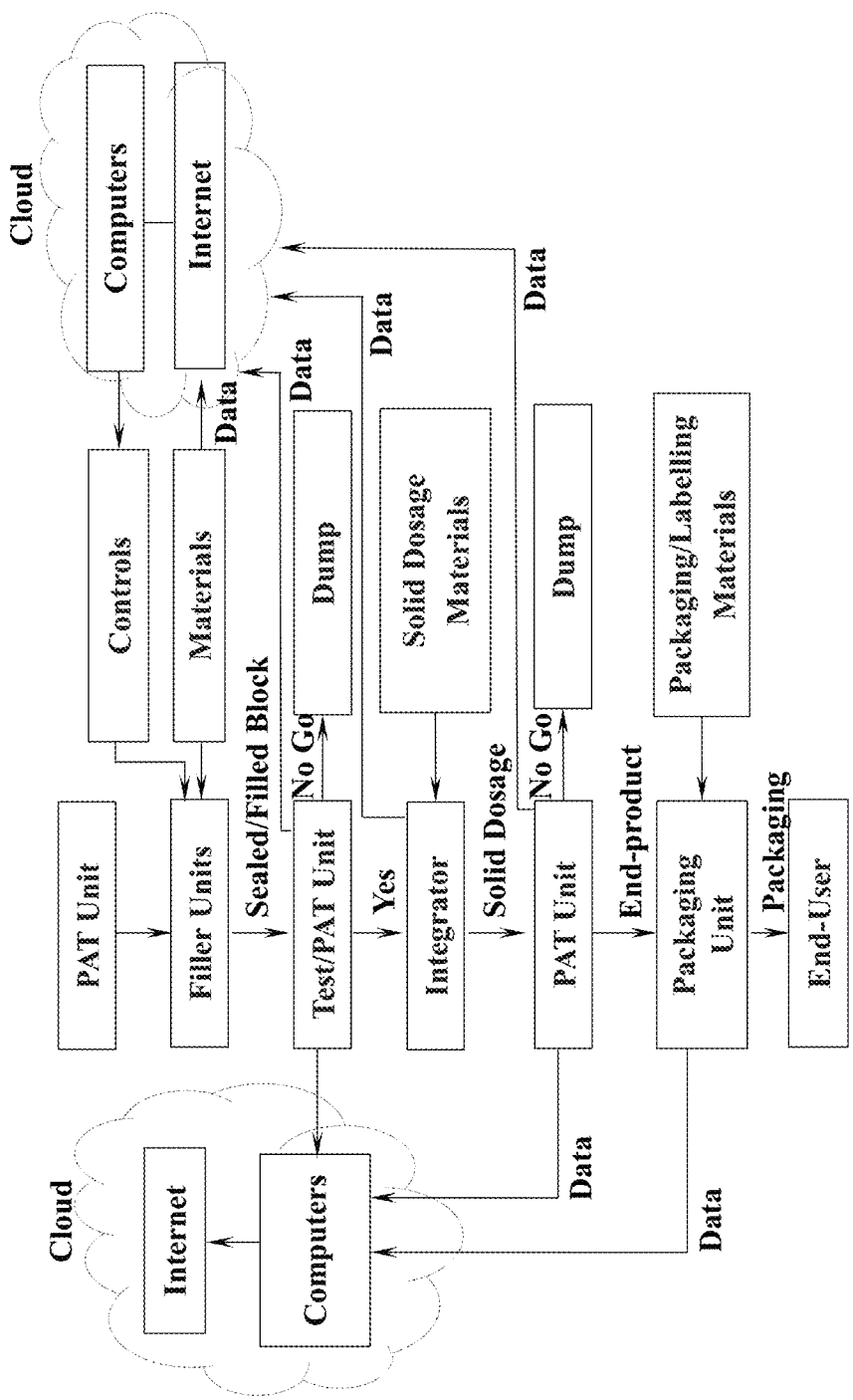
FIG. 10 is a flow diagram for the production of a solid dosage product in accordance with an aspect of the present invention.

As further shown in FIG. 9, multi-stage manufacturing systems may be executed by multiple globally distributed manufacturing facilities and/or companies. As a result, this approach introduces additional interfaces and interdependencies between participants as well as manufacturing and business processes. A product state-based view may offer structuring of product and process data for such already highly complex distributed manufacturing systems. In a production network, several entities may work together. Thus, any information exchanged is required to be in a format that all participants can derive and utilize within their individual systems. Thus, prior to its analysis, product state data is ideally not processed/interpreted and, therefore, exchangeable between various systems. Connecting the product state data to the individual product and process is consistent with increasing desire to ensure the quality of every single product, which is especially true for safety-critical products in pharmaceutical and medical devices industries. As shown in FIGS. 9 and 10, the product state may be derived at all times during a multi-stage manufacturing system. In order to design a manageable and sufficiently detailed model, the checkpoints when the product state should be derived have to be defined. In general, a higher number of defined product state checkpoints during a manufacturing program results in increased complexity and higher dimensionality of the model and a larger amount of data/information generated overall. Traditional estimation methods based on modelling cause-effect relationships are often ineffective in handling such added high-dimensionality and complexity well.

In solid dosage defect monitoring, the closeness of a tablet to a nominal tablet (a verified STA) according to a deviation measure/norm is tested and evaluated. Thus, various types of STAs may be designed to mimic various types of intra-process anomalies (acceptable or unacceptable) and defects. NIR, Raman scattering, and the acousto-vibrational/transient response of the tablet under a non-contact excitation may be used as a characteristic quantity. While current computational techniques may be useful in differentiating "good"/nominal tablets from defective tablets, these techniques provide limited information about the type of the defect (which might be helpful in assessing the defect) and its sources in the manufacturing chain. The most common defects are as follows: super or sub-potent formulations (excessive or insufficient active pharmaceutical ingredient) and foreign particle inclusion in tablets. However, many other types of minor, but typically acceptable, irregularities can develop in the intermediate process steps. The current art may not sense these irregularities until they compound upon themselves and lead to product rejections. In accordance with an aspect of the present invention, various STAs, such as that shown and described below with reference to FIGS. 15A-C using a phononic test artifact 600, have been developed to detect major and minor anomalies in real-time, thus possibility leading to prevention of undesirable manufacturing errors and product rejections.

Due to high-dimensionality and complexity concerns, it often makes sense for such cause-effect based approaches to choose as a substantially reduced number of checkpoints without reducing data fidelity excessively. It is a "rule-of-thumb" that at least as many checkpoints as there are processes needed to capture the primary product state changes. A checkpoint represents a critical control point which not only allows to assess the previous actions but to intervene in the process if necessary. In accordance with an aspect of the present invention, a method which utilizes combined Cluster Analysis (CA) and Supervised Machine Learning (SML) may be employed. Supervised learning and CA is suited to handle highly complex and high-dimensional data well. Analysis of this product and process state information/data describing the product state at the different checkpoints offers the chance to adjust process parameters of following processes accordingly during the manufacturing system. Therefore, the detected quality deviations of the final product should be minimized. Alternatively, identifying critical product state changes early in the manufacturing program may be used to implement a warning system that interferes if the product state changes in an unappreciated direction at a certain checkpoint early in the manufacturing program. Based on such a monitoring system, expert operators may then decide if the product can still reach the final quality requirements or if it should not receive more value adding processes.

Sequences of manufacturing operations and processes are characterized by the start and end states of each individual operation or process. Experiential data may be used to determine whether or not the states represent a desirable stage in the manufacturing of the product. An aspect of a method of the present invention may identify relevant drivers (causes) of certain product state changes in a practical and efficient way, without having to analyze or have in-depth knowledge of the cause-effect relations in detail. By way of example, process 30 as shown in FIG. 2 may have considerable complexity which generates high-dimensional data with unknown/unclear cause-effect relationships in and between individual process steps and with non-Gaussian data distributions. This data may exhibiting seeming chaotic behavior and include categorical or mixed (categorical and numerical) variables and numerical data with different scales of measurement. Furthermore, a monitoring technique without assumptions on the parametric forms of distributions is important in this context. In accordance with an aspect of the present invention, a combination of CA and SML may be introduced to handle the challenges discussed above and at the same time produce actionable/practical results.

Manufacturing processes exhibit states prior and subsequent to the process. In this context, the term process may be a unit operation or a sequence of operations in the manufacturing system. Such process states may be known/unknown/unknowable, desirable/undesirable and imply that some form of classification method would be required to monitor and ultimately facilitate process control. The problem arises with unknown and undesirable states. The unknown dimension could imply a prohibitively large set of states and as such would make classification infeasible. Assuming that there is a finite population of desirable states, it would be feasible to regard all other states as undesirable, and focusing on a finite set of states and the probability of the discovery of new desirable states as low. If it is assumed that the discovery of such new desirable states is possible, there exists a finite and relatively static population of desirable states. Thus, the manufacturing system exhibits a finite set of relatively static desirable states and all other states are by default undesirable. Based on this observation, a suitable classification method may be applied in order to calculate process states, and with the process state known, the basis for process monitoring and control may be established.

Choosing a classification method is an important step in implementation The dynamics of manufacturing processes often exhibit large dimensionality, non-Gaussian probabilistic responses, and (pseudo-)chaotic behavior. Simple classification methods often cannot guarantee providing a clear link between the classified state and state drivers, nor can it facilitate the determination of new states. Consequently, the applicability of methods such as first principle-based approaches, classical statistical process control and statistical dimension reducing methods is substantially limited, and the process complexity favors multi-variant methods and data-mining approaches. Moreover, linearization effects of the closed-loop controls implemented in sub-systems often force such complex systems into linear behavior (due to the nature of intrinsic control laws), thus reducing the risk of operating in zones with bifurcation in phase spaces. Classification methods, such as Support Vector Machine (SVM) and various forms of CA, could support the classification and new state discovery needs of large dimensionality process and product data.

CA is a systematic approach for finding structures in large data by identifying inherent clusters within the given data set. It is viewed as exploratory data analysis tools as it is generally used to generate, rather than test, hypotheses about data structures. In accordance with an aspect of the present invention, CA may be used to generate and iterate a learning set for use in the SML process. Constraining the manufacturing process sequence to a set of known and desirable states with the need to effect infrequent discovery of new desirable states, may provide the basis for a hybrid process monitoring and control approach which uses SML together with CA to handle the requirements of high-dimensionality data, unclear or unknown cause-effect mechanisms, non-Gaussian data with various scales and types. CA Unit indicates a continuous creation and updating of learning data, while Machine Learning Unit and Classifier indicate a real-time condition data capture and state classification and analysis. The product/process condition vectors $x_i$ form a population matrix X through time such that the population X is increasing incrementally with each process monitoring vector $x_i$. It is assumed that $x_i$ has high-dimensionality and that this process monitoring vector is captured in real-time. Real-time theoretically implies immediate reaction. In practice, the time horizon connected to real-time depends on the application. Real-time systems can react to certain events or triggers within an acceptable timeframe, such as hard real-time, where the task must be completed before a certain deadline, and soft real-time, where the task should be completed accordingly.

Production units may be interconnected using wireless communications and protocols that guarantee near real-time operation in addition to reliable data delivery. In particular, when transporting data from distributed production units to a private cloud or a remote computer, communication protocols need to be responsive to application-specific deadlines. The complete manufacturing program, which consists of the sequence of individual processes (unit operations), may therefore be seen as a sequence of classifiable states, and as the total manufacturing program progresses towards the conclusion, the state of the overall manufacturing program may be seen as the accumulated matrix "X". This matrix and the individual $x_i$ condition vectors thus form the working data for the classification methods. Once learning data has been established, incremental process state classification and monitoring may take place in real-time.

In learning phase, SML methods can handle large amounts of high-dimensionality data which create learning data that is used to create a model. In the model, the real-time monitoring vectors $x_i$ are processed to classify the implied state. Learning data can facilitate continuous learning. Such information is valuable as a process changes with time through wear and tear, maintenance, increased operator skills, and raw-material variability. In order to create the learning model it is necessary to identify characteristic data vectors and label these as representative for a state. Training is the initial phase for setting up the machine learning framework, and can subsequently be used to incorporate maturing and changing knowledge. Two complementing methods for achieving this objective are (i) clustering and (ii) adjustment by an expert (Machine Learning). The learning set Y consists of the learning vectors $y_i$. Each $y_i$ having the same format as the vectors $x_i$ except an additional label indicating which state it represents. In accordance with an aspect of the present invention, a set Y may be generated for STAs designed and printed each particular objective.

CA is the assignment of a set of observations into subsets (i.e., clusters), so that observations in the same cluster are similar in some sense. Clustering is a common method of unsupervised learning. It is used in Machine Learning, Data Mining and Pattern Recognition. Clustering techniques apply when there is no class to be predicted, but rather when the instances are to be divided into inherent groups. These clusters presumably reflect some mechanism at work in the domain from which instances are drawn, a mechanism that causes some instances to bear a stronger resemblance to each other than they do to the remaining instances. In producing obvious clusters, it is possible to name them and typify the cluster characteristics in terms of the implied process/product states. Consequently, the biggest gains are likely in knowledge-poor environments, particularly when there are large amounts of unlabeled, un-classified data. It is important to establish clusters that are a maximum distance apart as these would represent vectors that are the most different and as such are likely sources for learning data. Therefore, hierarchical cluster formation is considered suitable as a basis for selection of $y_i$ instances. Provided that hierarchical CA is used for the identification of candidate clusters for the learning data set, it is considered sufficient to complement the clustering with expert/user input.

Clustering information may be used to identify learning sets from the population X, so that clusters which exhibit 'extreme'/'undesirable'/'unusual' states different from the main mass of the population X may be included in a learning set for a Supervised Machine Learning method. This method is useful during continuing use of the process and for each product operation, so that by regular use of the CA Analysis of product state data, state knowledge can be updated through adjustments in the learning set. This phase may be run as frequently as needed to reflect the growing knowledge and/or increasing data variance.

In supervised learning and product/process states, as a starting point, Support Vector Machine (SVM) may be selected as the machine learning method. SVM methods build on developments in computational learning theory and is based upon the simple classification idea that an input set of values, vector $x_i$ is assigned to a positive class if $g(x_i) \geq 0$ where $g(x_i) = w \times x_i + b$, where the vector w represents the normal vector of a decision hyper-plane and is called the weight vector in SML. The hyper-plane thus described becomes the population separator, state classifier, of $x_i$, with $g(x_i)$ defining whether or not the $x_i$ is positively classified. SVM methods require learning data Y, which is typically compiled from selected process monitoring vectors $x_i$ or artificially created. The process monitoring vectors form time series and the aim is to determine the state of each process monitoring vector against Y. The learning data is furthermore an accurate representation of the data space, and placing a decision surface, hyper-plane, equidistant from the respective class/state boundaries should increase the probability of correctly classifying the data points ($x_i$) which are not included in Y, leading to the maximum margin SVM.

Once the learning data Y is established, the SVM process may then be employed to assess the state by classifying the process monitoring vector $x_i$. Given that $x_i$ is sampled as a time series, it is then possible to generate a state time series by classifying the $x_i$. SVM needs a relatively small sample set of data vectors by which to typify its states. X can also be used as a non-linear classifier, making it particularly useful. Furthermore, the binary nature of the SVM method may readily extend to a multi-class classifier. This approach allows the mapping of $x_i$ into a number of defined states with $g(x_i)$ indicating the strength of the membership of the state.

By constraining the product and associated manufacturing program monitoring to the observation of desirable and undesirable inter-process states, a hybrid monitoring and diagnosis method may be formed from CA coupled to SVM. SVM is regarded as being particularly suited for this purpose due to its reliable classification of high-dimensional data for real-time applications, while CA may assist in the definition of learning data. SVM may be applied to determine the process/product states at various points in the overall manufacturing program. The data may be analyzed to determine current drivers for a specific process/product state. A plot may then be generated with the y-axis showing the relative importance of process parameters, and the x-axis identifying the individual process parameter, where the greater the value is, the stronger the driver is. Negative values in this case, indicate that the parameter drives against the state membership and may assist in the diagnosis of the actual state and its corrective action.

It should be noted that while a method in accordance with the present invention has been shown and described as utilizing support vector machine learning with or without CA, other distributed prediction algorithms may be substituted or added, including without limitation solely thereto, Backpropagation Neural Networks (BPNNs), Feed Forward Neural Networks, Genetic Algorithms, Principal Component Analysis, decision trees, and Bayesian statistics.

Turning now to FIG. 9, a schematic drawing of an embodiment of a cyber-manufacturing machinery architecture 200 is shown. With the help of a production model 202, such as a calibration model block discussed below with regard to FIG. 11, which includes the specifications of the product (e.g., tablet 10) including at least one surface defining a plurality of compartments, each of the plurality of compartments formed to be located at a specific location on the at least one surface of the calibration model block and the production unit (e.g., manufacturing equipment) 204, and a variational mathematical model 206 programmed via software into a computing system for estimating the future states of the production unit 204 and the end-product (tablet 10), a central computer 208 may determine whether there is a need for required corrective actions 210 in all levels, such as from incoming materials 212 to performance of all components in the production unit 204. These corrective actions may also fed into central computer 208 to continuously improve the production model 202 so as to enable computer-controlled and monitored production of tablets 10. For instance, as further shown in FIG. 9, architecture 200 may be expanded such that central computer 208 may monitor and control any number of parallel production units 204 *a-n* so as to manufacture respective products 10 *a-n* from respective incoming materials 212 *a-i* n.

In FIG. 10, a flow diagram of production steps 300 of a production unit 204 used for production of an integrated solid dosage is depicted. PAT data generated for each product is transmitted to a central computer 208 via an Internet connection as described above. Also, the performance state of each production unit 204-204*n* is also transmitted to central computer 208 thereby allowing for not only the real-time monitoring of the product 10-10*n* properties and but also the state of its respective production unit 204-204*n*. These two data sets may then used to (i) determine the quality of the product and its real-time qualification and release, and (ii) monitor the state of all the production units in this integrated architecture.

Figure 11:
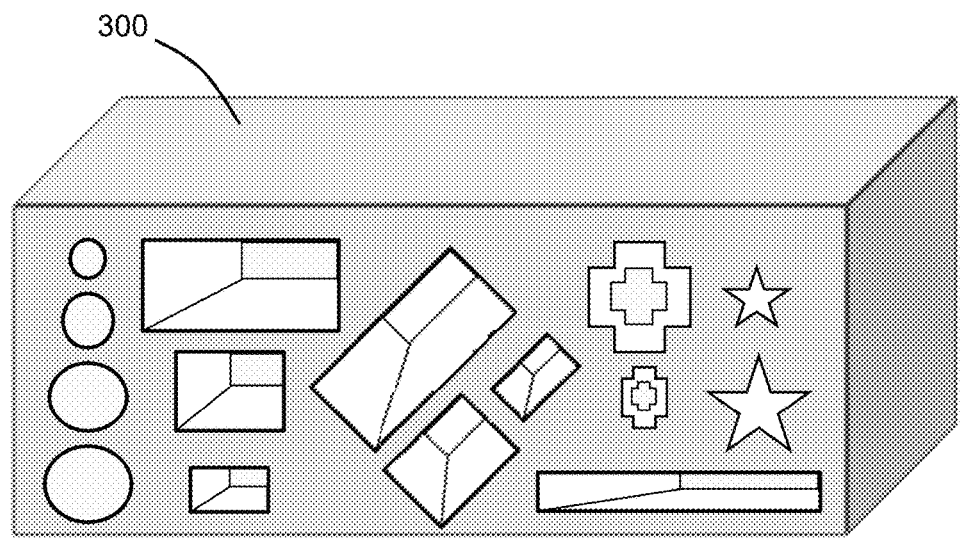
FIG. 11 is a calibration model of a carrier block in accordance with an aspect of the present invention.

In FIG. 11, an embodiment of a calibration model block 302 is shown. Calibration model block 302 may be used to test the performance of a production unit 204 (sub-systems, incoming materials, etc.) as shown in FIGS. 9 and 10. Calibration model block 302 may mimic a desired carrier block 100 and have features that are designed to test the performance of the production unit 204 which is manufacturing carrier block 100. Calibration model block 302 may also be used in actual simulated dissolution studies to determine the pharmacokinetics or pharmacodynamics of the API and filler materials involved in the design of the solid dosage product.

Figure 12:
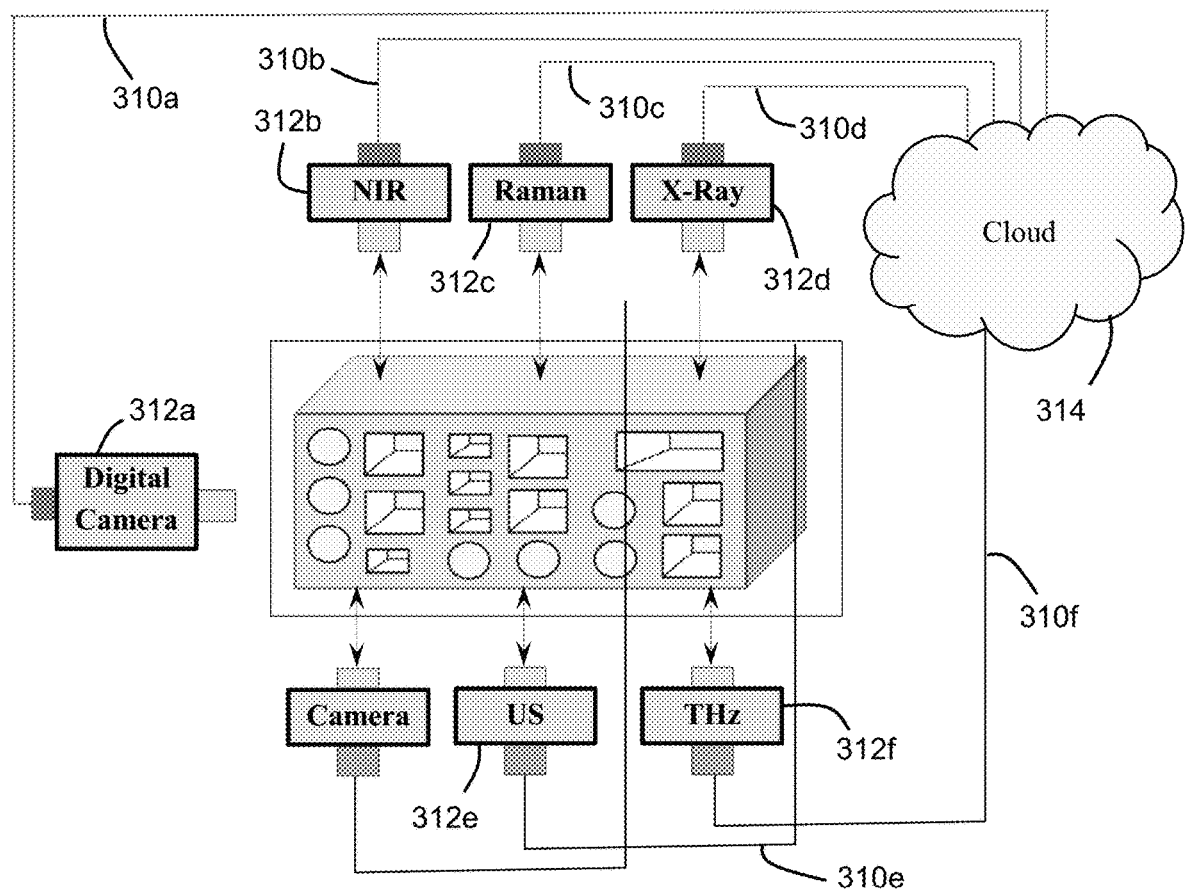
FIG. 12 is a schematic of an example showing monitoring of a carrier block in accordance with an aspect of the present invention.
Figure 13:
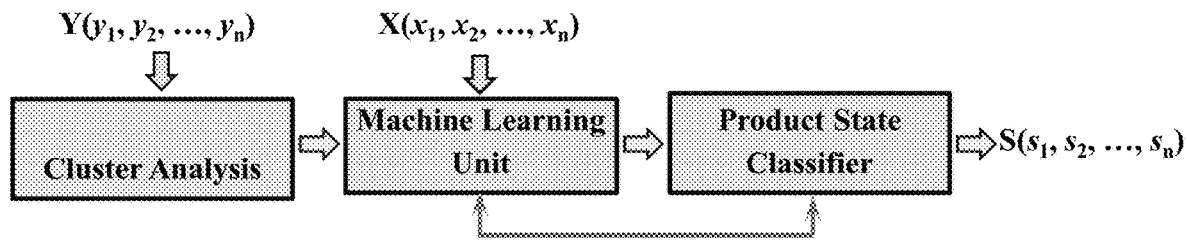
FIG. 13 shows process state monitoring using cluster analysis and supervised machine learning in accordance with an aspect of the present invention.

FIG. 12 depicts how various type of PAT tools, such as those described above, may be utilized to monitor the carrier block 100 before, during and after processing. The outputs 310*a-f* of the PAT tools 312*a-f* may be connected to Cloud or a remote computer 314. All computational functions such as data processing, computational tasks, computational analysis, data storage, data security, data access, sharing can be conducted in a secure computing facility and/or a set of local central computers, as shown in FIGS. 9 and 10. By way of example, the main phases of process state monitoring using CA and SML in a cloud implemented or a remote computing facility. Such an approach may require minimal local computing facilities implemented in the production machine thereby leading to a globally monitored and controlled production ability.

Figure 14:
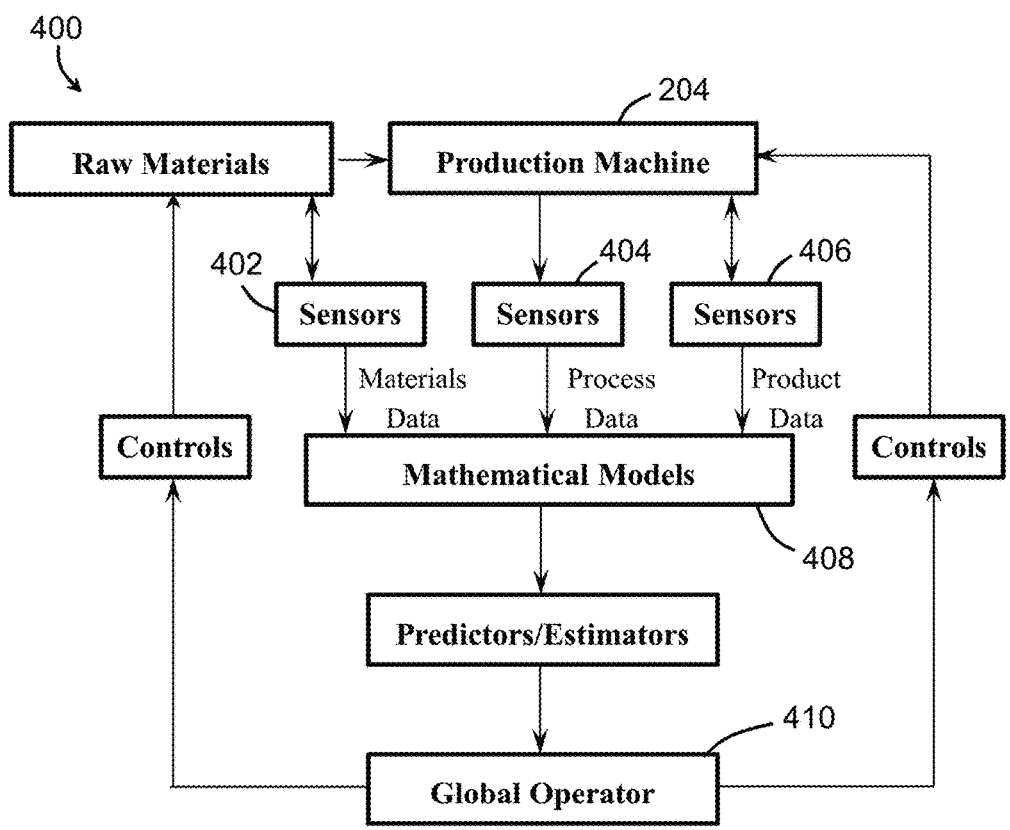
FIG. 14 shows a data analysis service framework in accordance with an aspect of the present invention.

In FIG. 14, a flowchart of the data analytics support framework 400 for process/product state monitoring over a computing service is shown. Data acquired from the process/product 402, materials property 404 and environmental sensors 406, as described above, may be fed to the mathematical models 408 serving to the state prediction/estimation utility in which distributed estimation and prediction models are implemented and their associated algorithms are run. Global Operator units 410 (implemented in a cloud or a remote computer) may provide feedback to the production 204 and its (human and/or machine) operators.

Figure 15A:
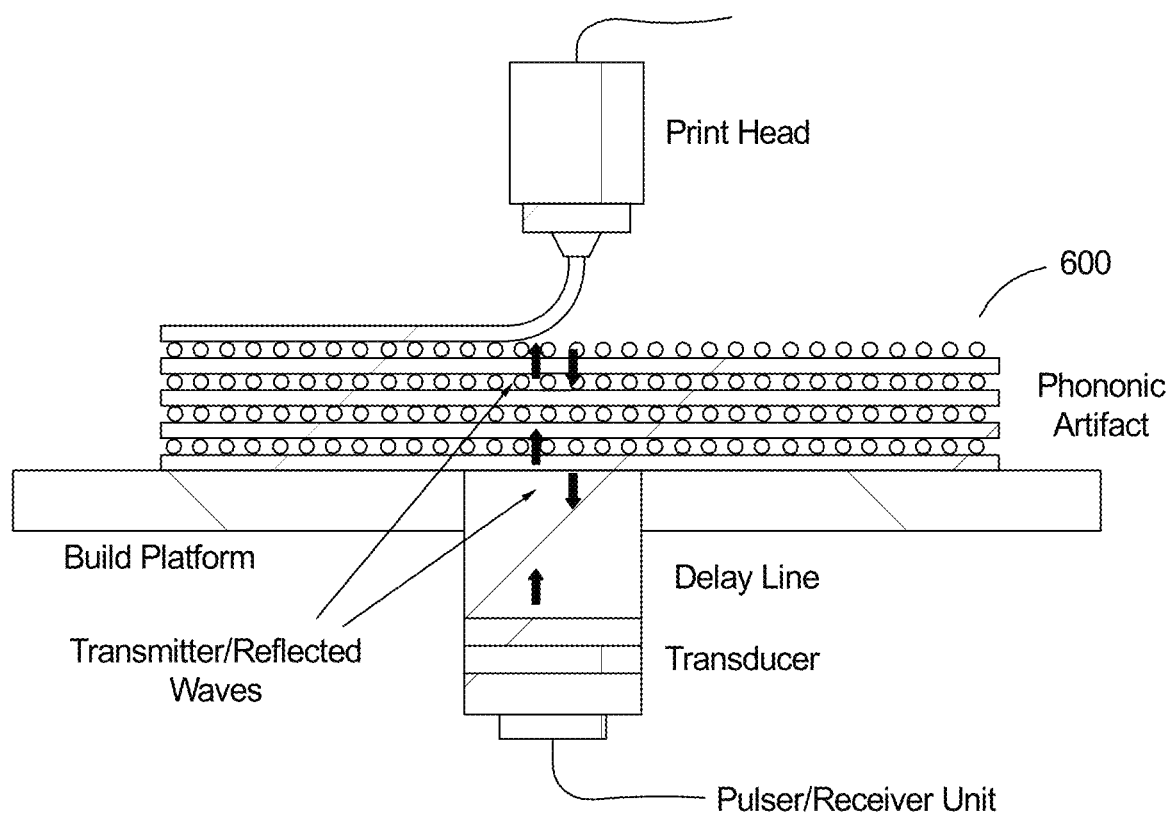
FIGS. 15A-15D show an exemplary phononic test artifact in accordance with an aspect of the present invention.
Figure 15B:
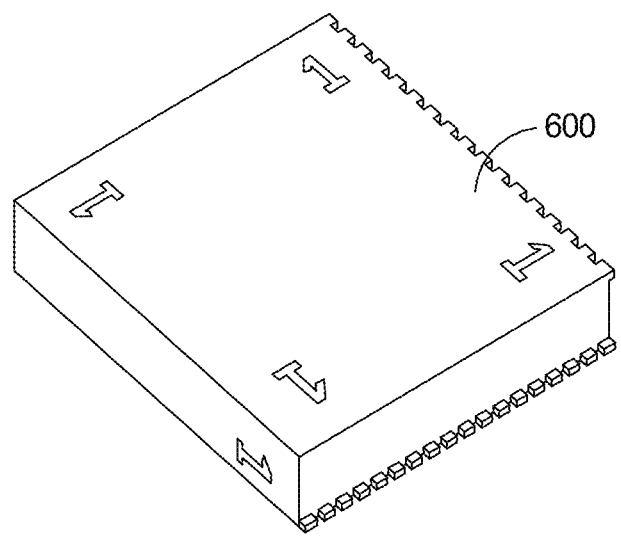
Figure 15C:
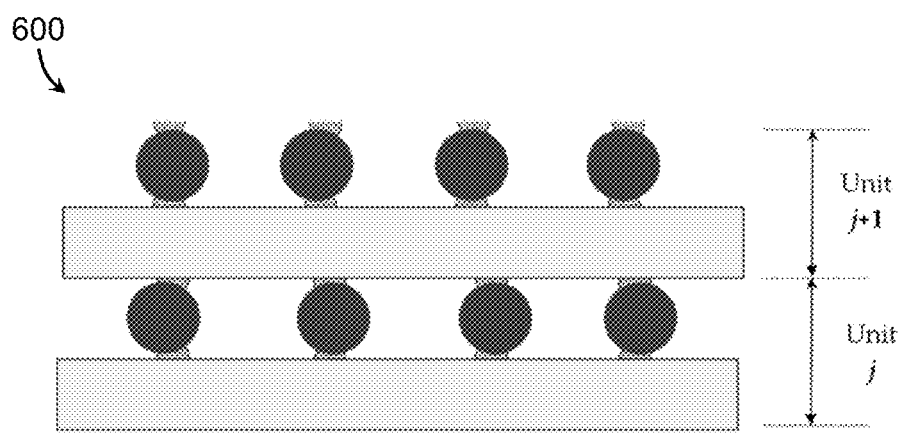
Figure 15D:
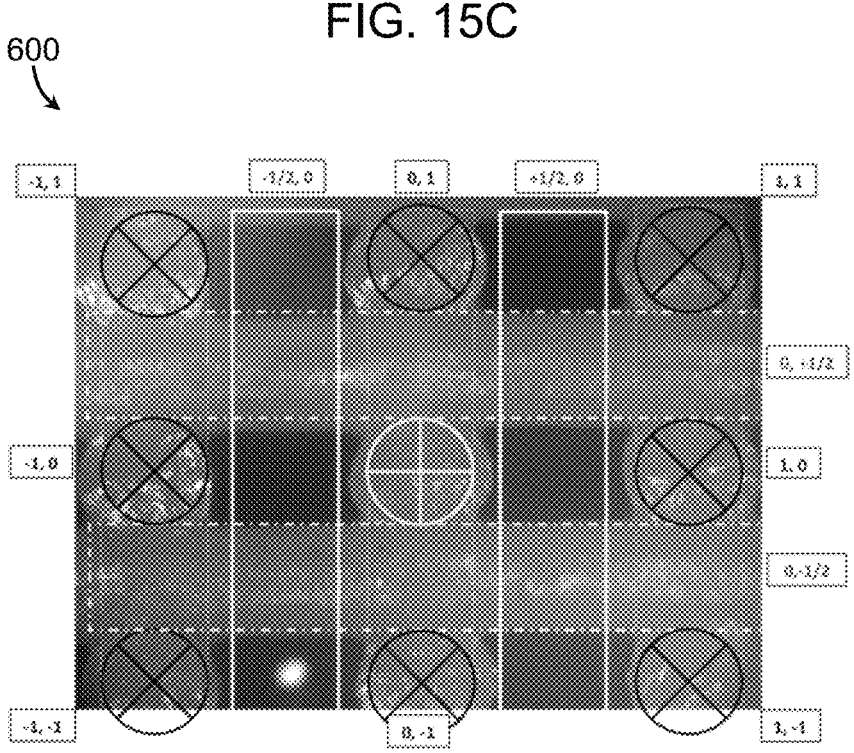
Figure 16A:
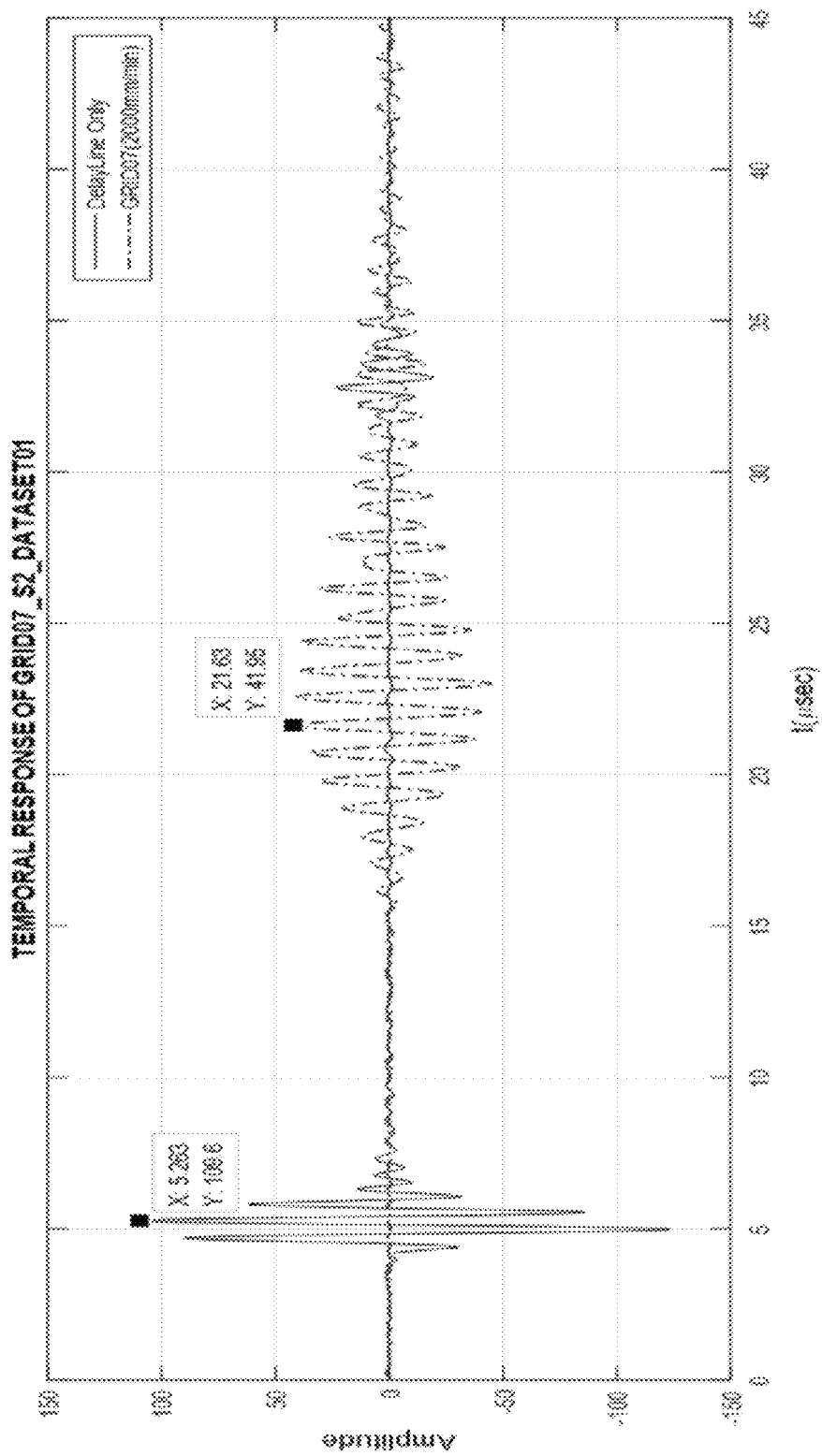
FIG. 16A shows the transient response of the phononic test artifact shown in FIG. 15B.
Figure 16B:
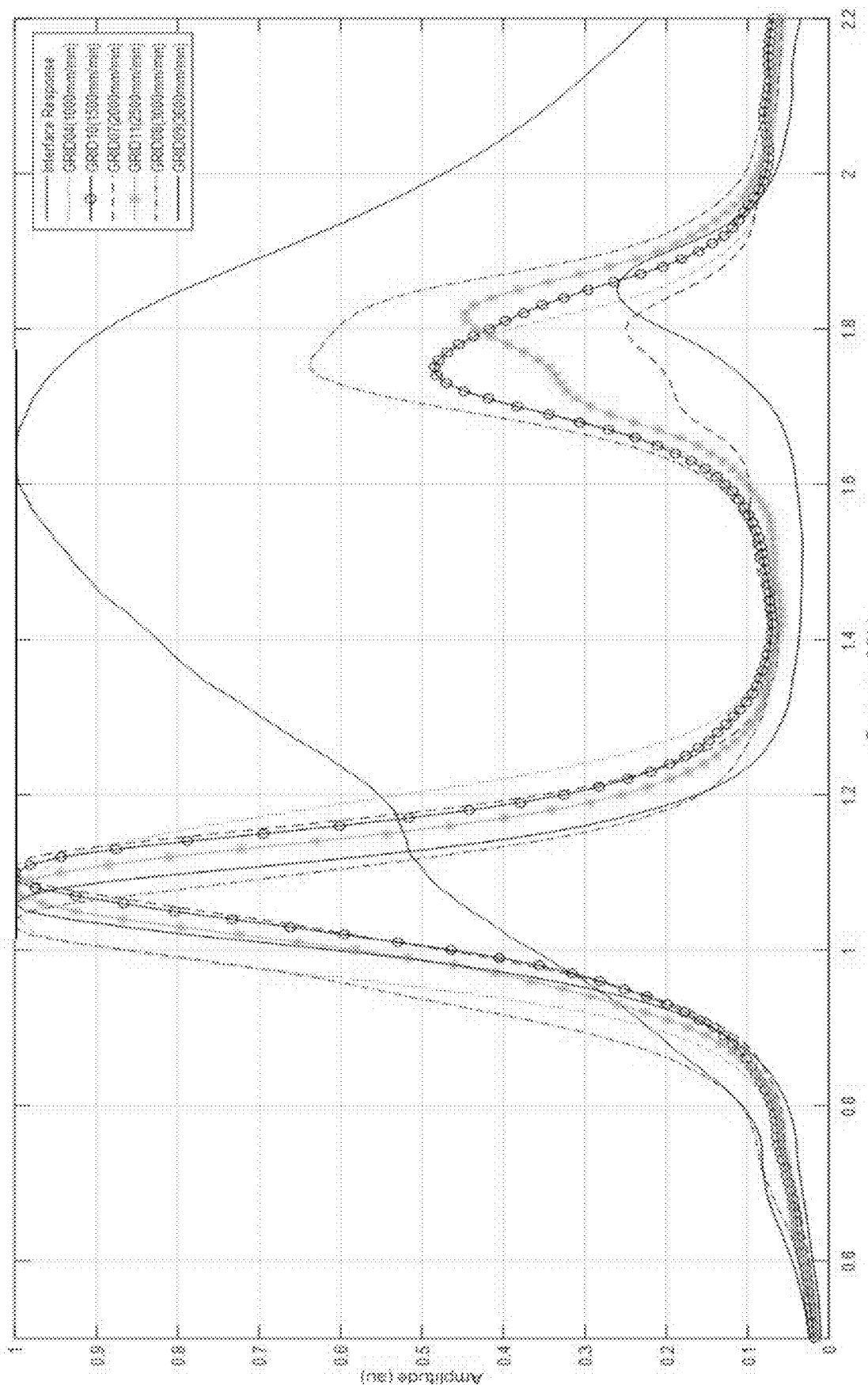
FIG. 16B shows the pass-stop bands of the phononic test artifact shown in FIG. 15B.

FIGS. 15A-D show an illustrative standardized test artifact (STA) for an exemplary phononic test artifact 600. FIG. 15A illustrates production of artifact 600 via a 3D printing operation while FIG. 15B is a photograph of a resultant artifact. FIGS. 15C and 15D show the internal microstructure of phononic test artifact 600 as formed by micron-scale filaments during the 3D printing process. FIG. 16A shows the transient response of phononic test artifact 600, while FIG. 16B shows the pass/stop bands of artifact 600, with a stop band around 1.4 MHz.

The foregoing description of the preferred embodiment of the invention has been presented for the purpose of illustration and description. It is not intended to be exhaustive nor is it intended to limit the invention to the precise form disclosed. It will be apparent to those skilled in the art that the disclosed embodiments may be modified in light of the above teachings. The embodiments described are chosen to provide an illustration of principles of the invention and its practical application to enable thereby one of ordinary skill in the art to utilize the invention in various embodiments and with various modifications as are suited to the particular use contemplated. Therefore, the foregoing description is to be considered exemplary, rather than limiting, and the true scope of the invention is that described in the following claims.

What is claimed is:

1. A solid dosage product having a tailored dissolution profile, the solid dosage product comprising:
   a) a carrier block including at least one surface, wherein the carrier block includes a plurality of compartments defined in the at least one surface, wherein each of the plurality of compartments is formed to be located at a specific location on the at least one surface of the carrier block, wherein the carrier block is constructed of a first material having a first dissolution profile, wherein at least one compartment of the plurality of compartments is further defined by a layer of a second material having a second dissolution profile which is different than the first dissolution profile, wherein each respective compartment is configured to selectively receive one or more active pharmaceutical ingredients therein and, wherein the carrier block is digestible within an animal such that each respective active pharmaceutical ingredient is controllably released; and
   b) one or more coating layers applied to the carrier block, wherein the carrier block and the one or more coating layers are configured for comparing to a calibration model block for quality monitoring and validation to verify that each of the plurality of defined compartments is formed at its respective specific location on the at least one surface the carrier block.

2. The solid dosage product of claim 1 wherein one or more electronic devices resides within a respective compartment of the plurality of compartments.

3. The solid dosage product of claim 2 wherein the one or more electronic devices is selected from the list consisting of a wireless transmitter, a remotely activated device, a logging device and a patient bonding device.

4. The solid dosage product of claim 1 wherein a respective active pharmaceutical ingredient comprises an active ingredient encapsulated by one or more excipients.

5. The solid dosage product of claim 4 wherein the active ingredient comprises about 75 percent of the respective active pharmaceutical ingredient.

6. The solid dosage product of claim 1 wherein the solid dosage product further includes one or more excipients, wherein the one or more excipients is contained within one or more of the carrier block, the one or more compartments or the one or more coating layers.

7. The solid dosage product of claim 1 wherein the one or more pharmaceutical ingredients is selected from the list consisting of a pellet, a powder, a liquid, an emulsion and a gel.

8. The solid dosage product of claim 1 wherein the first material is a digestible print material.

9. The solid dosage product of claim 1 wherein a respective pharmaceutical ingredient from said one or more active pharmaceutical ingredients is selected from the list consisting drugs, proteins, peptides, small molecules, nutritional supplements, vaccines and gene therapies.

10. The solid dosage product of claim 1 further comprising a solid dosage body, wherein the carrier block is incorporated within a portion of the solid dosage body.

* * * * *